United States Patent [19]
Ewen

[11] Patent Number: 5,846,896
[45] Date of Patent: *Dec. 8, 1998

[54] METALLOCENE CATALYST SYSTEMS

[75] Inventor: John A. Ewen, Houston, Tex.

[73] Assignee: Fina Technology, Inc., Dallas, Tex.

[*] Notice: The term of this patent shall not extend beyond the expiration date of Pat. No. 4,794,096.

[21] Appl. No.: 696,408

[22] Filed: May 6, 1991

Related U.S. Application Data

[63] Continuation of Ser. No. 317,089, Feb. 28, 1989, abandoned, which is a continuation of Ser. No. 256,163, Oct. 7, 1988, abandoned, which is a continuation of Ser. No. 34,472, Apr. 3, 1987, abandoned.

[51] Int. Cl.$^6$ ...................................................... B01J 31/00
[52] U.S. Cl. ............................ 502/117; 502/103; 502/112
[58] Field of Search ................................... 502/103, 112, 502/117

[56] References Cited

U.S. PATENT DOCUMENTS

| | | | |
|---|---|---|---|
| 4,522,982 | 6/1985 | Ewen | 525/240 |
| 4,530,914 | 7/1985 | Ewen et al. | 502/113 |
| 4,752,597 | 6/1988 | Turner | 502/117 X |
| 4,794,096 | 12/1988 | Ewen | 502/117 |
| 4,808,561 | 2/1989 | Welborn | 502/117 X |
| 4,892,851 | 1/1990 | Ewen et al. | 502/117 X |
| 4,937,299 | 6/1990 | Ewen et al | 526/119 |
| 5,077,255 | 12/1991 | Welborn | 502/117 |

*Primary Examiner*—Elizabeth D. Wood
*Attorney, Agent, or Firm*—Jim Wheelington; William D. Jackson; M. Norwood Cheairs

[57] ABSTRACT

A catalyst system for polymerization of olefins having increased molecular weight and melting point is disclosed. A chiral, stereorigid metallocene compound having a silicon hydrocarbyl compound as an interannular bridge between two cyclopentadienyl or substituted cyclopentadienyl rings described by the formula $(C_5R'_m)$ wherein R' is hydrogen or hydrocarbyl radical having from 1–20 carbon atoms, each R' being the same or different, is combined with an organoaluminum compound. The cyclopentadienyl ligands are coordinated with a metal of a group 4b, 5b, or 6b metal as designated in the Periodic Table of Elements. The metal is also bonded to a hydrocarbon radical or a halogen.

12 Claims, No Drawings

METALLOCENE CATALYST SYSTEMS

This is a continuation of application Ser. No. 07/317,089 filed on Feb. 28, 1989, now abandoned, which is a continuation of application Ser. No. 07/256,163 filed Oct. 7, 1988, now abandoned, which is a continuation of application Ser. No. 07/034,472, filed Apr. 3, 1987, now abandoned.

TECHNICAL FIELD

The present invention provides a method for varying the melting points and molecular weights of polyolefins in a process of polymerization using metallocene catalysts. The catalysts used in the present invention are chiral and stereorigid and include a bridge between the cyclopentadienyl groups. It has been discovered that changing the structure and composition of the bridge leads to changes in the melting points and molecular weights of the polymer products. It has also been discovered that addition of substituents to the cyclopentadienyl rings also influence these polymer properties. The present invention also includes the ability to control the melting points of polyolefins, particularly polypropylene, by controlling the number of inversions in the xylene insoluble fraction of the polymer chain.

BACKGROUND OF THE INVENTION

The present invention relates to the use of metallocene catalysts in the production of polyolefins, particularly polypropylene, and the ability to vary certain properties of the polymer products by varying the structure of the catalyst. In particular, it has been discovered that changes in the structure and composition of a bridge linking two cyclopentadienyl groups in the metallocene catalyst changes the melting points and the molecular weights of the polymer products.

The use of metallocenes as catalysts for the polymerization of ethylene is known in the art. German patent application 2,608,863 discloses a catalyst system for the polymerization of ethylene consisting of bis(cyclopentadienyl)-titanium dialkyl, an aluminum trialkyl and water. German patent application 2,608,933 discloses an ethylene polymerization catalyst system consisting of zirconium metallocenes of the general formula (cyclopentadienyl)$_n$ Zr Y$_{4-n}$, wherein Y represents R$_1$CH$_2$AlR$_2$, CH$_2$CH$_2$AlR$_2$ and CH$_2$CH (AlR$_2$)$_2$ wherein R stands for an alkyl or metallo alkyl, and n is used a number within the range 1–4; and the metallocene catalyst is in combination with an aluminum trialkyl cocatalyst and water.

The use of metallocenes as a catalyst in the copolymerization of ethylene and other alpha-olefins is also known in the art. U.S. Pat. No. 4,542,199 to Kaminsky, et al. discloses a process for the polymerization of olefins and particularly for the preparation of polyethylene and copolymers of polyethylene and other alpha-olefins. The disclosed catalyst system includes a catalyst of the formula (cyclopentadienyl)$_2$MeRHal in which R is a halogen, a cyclopentadienyl or a C$_1$–C$_6$ alkyl radical, Me is a transition metal, in particular zirconium, and Hal is a halogen, in particular chlorine. The catalyst system also includes an aluminoxane having the general formula Al$_2$OR$_4$(Al(R)-O)$_n$ for a linear molecule and/or (Al(R)—O)$_{n+2}$ for a cyclic molecule in which n is a number from 4–20 and R is a methyl or ethyl radical. A similar catalyst system is disclosed in U.S. Pat. No. 4,404,344.

U.S. Pat. No. 4,530,914 discloses a catalyst system for the polymerization of ethylene to polyethylene having a broad molecular weight distribution and especially a bimodal or multimodal molecular weight distribution. The catalyst system is comprised of at least two different metallocenes and an alumoxane. The patent discloses metallocenes that may have a bridge between two cyclopentadienyl rings with the bridge serving to make the rings stereorigid. The bridge is disclosed as being a C$_1$–C$_4$ alkylene radical, a dialkyl germanium or silicon, or an alkyl phosphine or amine radical.

European Patent Application 0185918 discloses a stereorigid, chiral metallocene catalyst for the polymerization of olefins. The bridge between the cyclopentadienyl groups is disclosed as being a linear hydrocarbon with 1–4 carbon atoms or a cyclical hydrocarbon with 3–6 carbon atoms. The application discloses zirconium as the transition metal used in the catalyst, and linear or cyclic alumoxane is used as a co-catalyst. It is disclosed that the system produces a polymer product with a high isotactic index.

It is known by those skilled in the art that polyolefins, and principally polypropylene, may be produced in various forms: isotactic, syndiotactic, atactic and isotactic stereoblock. Isotactic polypropylene contains principally repeating units with identical configurations and only a few erratic, brief inversions in the chain. Isotactic polypropylene may be structurally represented as

 (I)

Isotactic polypropylene is capable of forming a highly crystalline polymer with crystalline melting points and other desirable physical properties that are considerably different from the same polymer in an amorphous, or noncrystalline, state.

A syndiotactic polymer contains principally units of alternating configurations and is represented by the structure

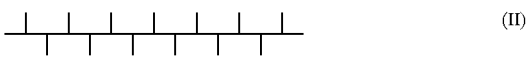 (II)

A polymer chain showing no regular order of repeating unit configurations is an atactic polymer. In commercial applications, a certain percentage of atactic polymer is typically produced with the isotactic form. It is highly desirable to control the atactic form at a relatively low level.

A polymer with recurring units of opposite configuration is an isotactic stereoblock polymer and is represented by

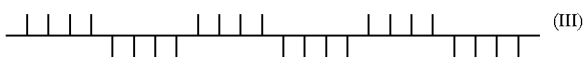 (III)

This latter type, the stereoblock polymer, has been successfully produced with metallocene catalysts as described in U.S. Pat. No. 4,522,982.

It may also be possible to produce true block copolymers of isotactic and atactic forms of polyolefins, especially polypropylene.

A system for the production of isotactic polypropylene using a titanium or zirconium metallocene catalyst and an alumoxane cocatalyst is described in "Mechanisms of Stereochemical Control in Propylene Polymerization with Soluble Group 4B Metallocene/Methyalumoxane Catalysts," J. Am. Chem. Soc., Vol. 106, pp. 6355–64, 1984. The article shows that chiral catalysts derived from the racemic enantiomers of ethylene-bridged indenyl derivatives form isotactic polypropylene by the conventional structure predicted by an enantiomorphic-site stereochemical control model. The meso achiral form of the ethylene-bridged titanium indenyl diastereomers and the meso achiral zirconocene derivatives, however, produce polypropylene with a purely atactic structure.

Further studies on the effects of the structure of a metallocene catalyst on the polymerization of olefins was reported in "Catalytic Polymerization of Olefins," Proceedings of the International Symposium on Future Aspects of Olefin Polymerization, pp. 271–92, published by Kodansha Ltd., Tokyo, Japan, 1986. In this article, the effects of the chiralities, steric requirements and basicities of ligands attached to soluble titanium and zirconium metallocene catalysts on the polymerization and copolymerization of propylene and ethylene were reviewed. The studies revealed that the polymerization rates and molecular weights of the polymers obtained in the polymerization of ethylene with a zirconocene catalyst vary according to the basicity and steric requirements of the cyclopentadienyl groups. The effects of ligands also contributed to the synthesis of polypropylenes with novel microstructures and high density polyethylenes with narrow and bimodal molecular weight distributions.

The present invention relates to discoveries made as to varrying the bridge structure and substituents added to the cyclopentadienyl rings in a metallocene catalyst on the polymerization of propylene and high alpha-olefins. In particular, it was discovered that by varying these components, the physical properties of the polymer may be controlled.

SUMMARY OF THE INVENTION

As part of the present invention, it was further discovered that the number of inversions in the xylene insoluble fraction may be varied by changing the components that form the bridge between the cyclopentadienyl rings in a metallocene catalyst. It was also discovered that the addition of various substituents on the cyclopentadienyl rings also varied the number of inversions. Thus, a means for varying the melting point of a polyolefin was discovered. This is a significant discovery, as heretofore it was the commercial practice to vary the melting points of polymer products by co-polymerizing varying amounts of ethylene to produce co-polymers with a range of differing melting points. It is desirable to produce a homopolymer with varying melting points without the use of ethylene. The present invention provides a method for the production of homo-polymers with varying melting points by varying the structure of the metallocene catalyst used in the polymerization.

Similarly, it was discovered-that by changing the structure of the metallocene catalyst, polymers are produced with varying molecular weights. Thus, the molecular weight of the polymer product may be varied by changing the catalyst. Accordingly, the present invention provides a method for varying both the melting point and the molecular weight of a polymer product.

The present invention also provides a process for the polymerization of olefins comprising contacting an organoaluminum compound with a metallocene described by the formula:

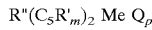

wherein $(C_5R'_m)$ is a cyclopentadienyl or substituted cyclopentadienyl ring; R' is a hydrogen or a hydrocarbyl radical having from 1–20 carbon atoms, each R' may be the same or different; R" forms a bridge between the two $(C_5R'_m)$ rings and contains a bridge group consisting of an alkylene radical having 1–4 carbon atoms, a silicon hydrocarbyl compound, a germanium hydrocarbyl compound, an alkyl phosphine, an alkyl amine, a boron compound or an aluminum compound, and any of these bridge groups may contain any of these or other hydrocarbyl groups attached to the bridge; Q is a hydrocarbon radical such as an alkyl, aryl, alkenyl, alkylaryl or arylalkyl radical having 1–20 carbon atoms or is a halogen; Me is a group 4b, 5b or 6b metal as positioned in the Periodic Table of Elements; $0 \leq m \leq 4$; and $0 \leq p \leq 3$. An olefin monomer is added to the metallocene catalyst and the organoaluminum compound. After the polymerization has taken place, the polymer product is withdrawn. The process is characterized by the fact that it provides control of the melting point of the polymer product by controlling the number of inversions in the xylene insoluble fraction of the polymer. The number of inversions are effected by the R" group and the R' group. Thus, the melting point of the polymer product may be varied and controlled by varying the R" bridge and/or the R' substituents on the cyclopentadienyl rings.

The present invention also provides a method for varying the melting points of polymer products and a method for varying the molecular weights of the polymer products. These methods include the use of the metallocene catalyst described by the above formula. The melting points and molecular weights of the polymer products are varied by changing the R" bridge and/or the R' substituents on the cyclopentadienyl rings.

DETAILED DESCRIPTION

The present invention provides a method of controlling the melting point of a polymer by controlling the number of inversions in the chain of the xylene insoluble fraction of the polymers. The number of inversions are controlled in turn by the structure and composition of the catalyst, and the number of inversions and hence the melting point of the polymer product may be controlled and varied by varying the catalyst. In particular, it has been discovered that varying the R" bridge between the cyclopentadienyl rings will vary the melting point of the polymer product. Varying the R' substituents on the rings will also vary the melting point. In addition, it has been discovered that varying the R" bridge and/or the R' substitutents in the catalyst will also vary the molecular weights of the polymer products. These beneficial advantages will become more apparent from the following detailed description of the invention and the accompanying examples.

Normally, when propylene, or another alpha-olefin, is polymerized in a catalyst system prepared from a transition metal compound, the polymer comprises a mixture of amorphous atactic and crystalline xylene insoluble fractions which may be extracted using suitable solvents. Transition metal catalysts in the form of metallocenes have been known for some time, but up until just recently, such catalysts could only produce predominantly atactic polymer which is not nearly as useful as the isotactic form. It was discovered that by attaching a bridge between the cyclopentadienyl rings in a metallocene catalyst and by adding one or more substituents on the rings to make the compound both stereorigid and chiral, a high percentage of isotactic polymer could be produced. As described by the present invention, the composition of the bridge and the substituents added to the rings affect the properties of the polymer such as melting points and molecular weights.

The metallocene catalyst as used in the present invention must be chiral and stereorigid. Rigidity is achieved by an interannular bridge. The catalyst may be described by the formula:

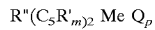

wherein $(C_5R'_m)$ is a cyclopentadienyl or substituted cyclopentadienyl ring; R' is a hydrogen or a hydrocarbyl radical having from 1–20 carbon atoms, each R' may be the same or different; R" is the bridge between the two ($C_5R'_m$) rings and is an alkylene radical having 1–4 carbon atoms, a silicon hydrocarbyl radical, a germanium hydrocarbyl radical, an alkyl phosphine, or an alkyl amine; Q is a hydrocarbon radical such as an alkyl, aryl, alkenyl, alkylaryl or arylalkyl radical having 1–20 carbon atoms or is a halogen; Me is a group 4b, 5b or 6b metal as positioned in the Periodic Table of Elements; $0 \leq m \leq 4$; and $0 \leq p \leq 3$.

Exemplary hydrocarbyl radicals are methyl, ethyl, propyl, butyl, amyl, isoamyl, hexyl, isobutyl, heptyl, octyl, nonyl, decyl, cetyl, phenyl, and the like. Exemplary alkylene radicals are methylene, ethylene, propylene and the like. Exemplary halogen atoms include chlorine, bromine and iodine with chlorine being preferred.

The preferred transition metals are titanium, zirconium and hafnium. Q is preferably a halogen and p is preferably 2. R' is preferably a phenyl or cyclohexyl group such that ($C_5R'_m$) forms an indenyl radical which may be hydrated. As indicated, other hydrocarbon groups may be added to the cyclopentadienyl rings. The preferred R" bridge components are methylene (—$CH_2$—), ethylene (—$C_2H_4$—), an alkyl silicon and a cycloalkyl silicon such as cyclopropyl silicon, among others. The present invention is such that the R" bridge and the R' substituents may be varied among any of those compounds listed in the above formula so as to provide polymer products with different properties.

The metallocene catalysts just described are used in combination with an organoaluminum compound. Preferably, the organoaluminum compound is an alumoxane represented by the general formula (R—Al—O)n in the cyclic form and R(R—Al—O—)$_n$AlR$_2$ in the linear form. In the general formula, R is an alkyl group with 1–5 carbons and n is an integer from 1 to about 20. Most preferably, R is a methyl group. Generally, in the preparation of alumoxanes from, for example, trimethyl aluminum and water, a mixture of the linear and cyclic compounds are obtained.

The alumoxanes can be prepared in various ways. Preferably, they are prepared by contacting water with a solution of trialkyl aluminum, such as, for example, trimethyl aluminum, in a suitable solvent such as benzene. Most preferably, the alumoxane is prepared in the presence of a hydrated copper sulfate as described in U.S. Pat. No. 4,404,344 the disclosure of which is hereby incorporated by reference. This method comprises treating a dilute solution of trimethyl aluminum in, for example, toluene with copper sulfate represented by the general formula $CuSO_4.5H_2O$. The reaction is evidenced by the production of methane.

The metallocene catalysts used in the present invention are produced using methods known to those skilled in the art. Typically, the procedures simply comprise the addition of the MeQ groups described above and the R" group to a starting compound such as indene or some other substituted dicyclopentadiene.

The polymerization procedures useful in the present invention include any procedures known in the art. An example of a preferred procedure would be that disclosed in U.S. Pat. No. 4,767,735, issued Aug. 30, 1988, hereby incorporated by reference which describes a prepolymerization of the catalyst before introducing the catalyst into a polymerization reaction zone.

In the Examples given below, three different polymerization procedures were utilized. These procedures, designated as A, B and C are described as follows:

Procedure A

A dry two liter stainless steel Zipperclave was utilized as the reaction vessel and was purged with 2 psig of nitrogen. An alumoxane solution was introduced into the reaction vessel using a syringe which was followed by the introduction of the metallocene catalyst solution by a second syringe. Approximately, 1.2 liters of propylene are added at room temperature and then heated to the run temperature in 2–5 minutes was then added to the reaction vessel, and the agitator was set at 1200 rpm. The temperature of the reaction vessel was maintained at the run temperature. After 1 hour of stirring, the agitator was stopped, the propylene was vented, and 500 ml of either heptane or toluene was added using nitrogen pressure. The reactor was stirred for 5 minutes and then the contents were poured into a beaker containing 300 ml of a 50/50 solution of methanol/4N HCl. After stirring for 30 minutes, the organic layer was separated, washed 3 times with distilled water, and poured into an evaporating dish. After evaporating the solvent, the remaining polymer was further dried in a vacuum oven.

Procedure B

The procedure is similar to Procedure A except that 1.0 liter of propylene was first added to the reactor. The alumoxane and catalyst were added to a 75 cc stainless steel sample cylinder and allowed to precontact for several minutes before being flushed to the reactor with 0.2 liters of propylene. The remaining procedures were as described in A.

Procedure C

Into a dry 500 cc stainless steel Zipperclave was added 120 cc of dry toluene and the temperature set at the designated run temperature. The alumoxane solution was syringed into the reactor followed by the addition of the catalyst solution by syringe. About 120 cc of propylene was then added to the reactor using nitrogen pressure. After one hour of agitation and temperature control, the agitator was stopped and the propylene vented. The polymer was then extracted as described in A.

These are just examples of possible polymerization procedures as any known procedure may be used in practicing the present invention.

The polymer product may be analyzed in various ways for differing properties. Particularly pertinent to the present invention are analyses for melting points, molecular weights, and inversions in the chain.

The melting points in the examples below were derived from DSC (Differential Scanning Calorimetry) data as known in the art. The melting points reflected in the tables are not true equilibrium melting points but are DSC peak temperatures. With polypropylene it is not unusual to get an upper and a lower peak temperature, i.e., two peaks, and the data reflects the lower peak temperature. True equilibrium melting points obtained over a period of several hours would be 5°–12° C. higher than the DSC lower peak melting points. The melting points for polypropylenes are determined by the crystallinity of the xylene insoluble fraction of the polymer. This is shown to be true by running the DSC melting points before and after removal of the xylene solubles or atactic form of the polymer. The results showed only a difference of 1°–2° C. in the melting points after most of the atactic polymer was removed and isotactic polymer remained. The xylene insoluble fraction of the polymer yields a sharper and more distinct melting point peak.

NMR analysis was used to determine the exact microstructure of the polymer including the mole fraction of inversions in the chain of the xylene insoluble fraction. The NMR data may be actually observed or it may be calculated using statistical models. NMR analysis is used to measure the weight percent of atactic polymer and the number of inversions in the xylene insoluble fraction of the polymer.

The molecular weights of the xylene insoluble fractions of the polymers were calculated using GPC (Gel Permeation Chromatography) analysis. For the examples given below, the analysis was done on a Waters 150 C instrument with a column of Jordi gel and an ultra high molecular weight mixed bed. The solvent was trichlorobenzene and the operating temperature was 140° C. From GPC, $M_w$, or the weight average molecular weight, and $M_n$ are obtained. $M_w$ divided by $M_n$ is a measurement of the breadth of the molecular weight distribution.

As known in the art, the molecular weight of a polymer is proportional to the rate of propagation of the polymer chain divided by the rate of termination of the chain. A change in the ratio leads to a change in the molecular weights. As described by the present invention, a change in the structure of the catalyst leads to a change in the ratio of the rates of polymerization as well as a change in the melting points of the polymer.

The following Examples illustrate the present invention and its various advantages in more detail. The Examples use various zirconocenes to illustrate the invention but similar results would be expected using titanocene, hafnocenes and other metallocene catalysts. The results are summarized in Table 1.

EXAMPLE 1

The polymerization of propylene was carried out using 3 mg of ethylenebis(indenyl)zirconium dichloride as the catalyst and using polymerization Procedure B as outlined above. Enough alumoxane was used to produce a Al/Zr metal atom ratio of 1.4 mol Al/mmol of Zr. The reaction temperature was 30° C. The polymerization produced a yield of 51.0 grams of polypropylene which results in an efficiency of 17.0 kg of polypropylene/g of catalyst in 1 hour (kg/g.cat.1 h). Atactic polymer was removed by dissolving the polymer product in hot xylene, cooling the solution to 0° C., and precipitating out the isotactic form. The intrinsic viscosity of the xylene insoluble fraction was calculated to be 0.495 dl/gm from measurements taken on a Differential Viscometer in decalin at 135° C. The GPC analysis showed a $M_w$ of 40,000 and a $M_w/M_n$ of 2.2 for the xylene insoluble or xylene insoluble fraction. The results are summarized in Table 1.

EXAMPLE 2

Polymerization Procedure C as described above was used with 2.00 mg of ethylenebis(indenyl)zirconium dichloride as the catalyst. The Al/Zr ratio was 2.1 (mol/mmol) and the reaction temperature was 50° C. In addition to the analyses performed in Example 1, DSC analysis for a peak temperature or melting point ($T_m$) of the xylene insoluble fraction and analysis of the NMR spectrum for the mole fraction of inversions in the isotaction fraction in the chain were performed. The results are shown in Table 1.

EXAMPLE 3

Polymerization Procedure A as described above was used with 0.6 mg of ethylenebis(indenyl)zirconium dichloride as the catalyst. The Al/Zr ratio was 7.0 (mol/mmol) and the reaction temperature was 50° C. The results of the polymerization and analysis are shown in Table 1.

EXAMPLE 4

The procedures of Example 3 were repeated except that 1.43 mg of catalyst were used, the Al/Zr ratio was 2.9 (mol/mmol) and the reaction temperature was 80° C. A tremendous increase in the yield and efficiency of the catalyst were obtained. The results are shown in Table 1.

EXAMPLES 5–8

In these Examples, the catalyst used was ethylenebis(4,5,6,7-tetrahydro-1-indenyl)zirconium dichloride, the tetrahydrated form of the catalyst used in Examples 1–4. This was done in order to demonstrate the effect of a different substituent on the cyclopentadienyl rings. The polymerization runs were carried out using varying procedures, catalyst amounts, Al/Zr ratios, and temperatures as indicated in Table 1. The results in Table 1 show a different range of melting points ($T_m$) and molecular weights ($M_w$) as the catalyst was hydrogenated.

EXAMPLES 9–11

These Examples used a zirconocene catalyst with a dimethyl silicon bridge instead of an ethylene bridge. The catalyst used was dimethylsilylbis(indenyl)zirconium dichloride. The polymerization conditions and results are shown in Table 1. With the substitution of a silicon bridge for an ethylene bridge, the melting points and molecular weights increased.

EXAMPLES 12–17

These Examples used a catalyst with a cyclopropyl group attached to a silicon bridge—thus the catalyst was cyclopropylsilylbis(indenyl)zirconium dichloride. The polymerization conditions and results are shown in Table 1. Slightly higher melting points and molecular weights were obtained with this structure of catalyst.

EXAMPLE 18

In this example, a zirconocene catalyst with a larger bridge structure was used; the catalyst used was 1,1,4,4,-tetramethyl-disilylethylenebis(indenyl)zirconium dichloride in the amount of 1.45 mg. The Al/Zr ratio was 6.0 mol/mmol and the reaction temperature was 50° C. The reaction was run for an hour, but no significant amount of polypropylene was formed. In other tests, this catalyst was shown useful in the polymerization of ethylene and a copolymer of ethylene and propylene.

TABLE 1

| Example | Poly. Proc. | Cat. mg. | Al/Zr mol/mmol | Temp. °C. | Yield gms | Efficiency kg/g · cat · 1 h | Tm °C. DSC Peak | Mole Percent of Inversions in Isotactic Fraction | I.V. dl/gm | Mw/1000 | Mw/Mn |
|---|---|---|---|---|---|---|---|---|---|---|---|
| 1 | B | 3.0 | 1.4 | 30 | 51.0 | 17.0 | 140 |  | 0.50 | 40 | 2.2 |
| 2 | C | 2.0 | 2.1 | 50 | 20.0 | 12.7 | 135.2 | 2.5 | 0.23 |  |  |

TABLE 1-continued

| Example | Poly. Proc. | Cat. mg. | Al/Zr mol/mmol | Temp. °C. | Yield gms | Efficiency kg/g · cat · 1 h | Tm °C. DSC Peak | Mole Percent of Inversions in Isotactic Fraction | I.V. dl/gm | Mw/1000 | Mw/Mn |
|---|---|---|---|---|---|---|---|---|---|---|---|
| 3 | A | 0.6 | 7.0 | 50 | 25.4 | 33.3 | 135.3 | | 0.33 | 23 | 2.2 |
| 4 | A | 1.43 | 2.9 | 80 | 221.0 | 154.5 | 125.6 | 4.5 | 0.23 | 14 | 2.1 |
| 5 | A | 19.6 | 0.2 | 20 | 16.5 | 0.8 | 143.0 | 1.2 | 0.39 | | |
| 6 | B | 49.9 | 0.1 | 10 | 13.0 | 0.3 | 139.7 | | 0.42 | 29 | 3.5 |
| 7 | A | 1.86 | 2.3 | 50 | 33.0 | 17.7 | 136.8 | | 0.18 | 11 | 2.3 |
| 8 | A | 3.38 | 1.3 | 80 | 265.0 | 78.4 | 120.9 | | 0.10 | | |
| 9 | A | 3.5 | 1.3 | 30 | 8.7 | 2.5 | 145.2 | | 0.61 | 50 | 2.2 |
| 10 | C | 2.0 | 2.2 | 50 | 64.0 | 32.0 | 142.3 | 1.6 | 0.46 | 36 | 2.3 |
| 11 | A | 0.7 | 6.4 | 80 | 20.5 | 29.3 | 135.3 | 3.1 | 0.27 | 18 | 2.2 |
| 12 | B | 10.0 | 0.5 | 30 | 1.8 | 0.2 | 146.7 | | 0.41 | | |
| 13 | B | 1.0 | 4.6 | 30 | 6.0 | 6.0 | | | 0.55 | | |
| 14 | B | 3.1 | 1.5 | 50 | 1.8 | 0.6 | 141.5 | | 0.40 | 30 | 3.4 |
| 15 | B | 1.0 | 4.6 | 50 | 14.0 | 14.0 | | | 0.48 | | |
| 16 | A | 2.89 | 1.6 | 80 | 5.8 | 2.0 | 138.2 | | 0.36 | 26 | 2.7 |
| 17 | B | 2.50 | 1.8 | 80 | 69.0 | 27.6 | | | 0.41 | | |
| 18 | B | 1.45 | 6.0 | 50 | 0 | 0 | | | | | |

The results shown in Table 1 illustrate some of the advantages of the present invention. The substituents on the cyclopentadienyl rings and the compositions and structures of the bridge between the rings do have a significant influence on the stereoregularities, melting points and the molecular weights of the polymers. These effects are a result of the steric and electronic properties of the substituents and bridge structures.

It is noted that the polymerization temperature is a factor in the formation of the polymer product. At the lower reaction temperatures, the melting points and molecular weights for the same catalyst were higher. As the reaction temperatures increased, the melting points and the molecular weights decreased. Also, as the reaction temperature increased, the yields and catalyst efficiencies also increased, usually dramatically.

Some of the advantages of the present invention are realized by comparing the polymer properties of Examples using different catalysts but run at the same polymerization temperature. In making these comparisons, it can be seen that the melting points increased and the mole fraction of inversions decreased as the R" bridge structure was changed from ethylene to an alkyl silicon bridge. The molecular weights also increased as silicon was substituted for ethylene. The results show that polymers with lower molecular weights are produced by catalysts with more bulky and more basic ligands. Also, some increase was noted as the indenyl groups were hydrated. Thus, the more electron dontaing that the R' and R" groups are, the molecular weights of the products can be expected to be higher. The results clearly show that the melting points and molecular weights can be varied by changing the bridge structure and the substituent groups in the cyclopentadienyl rings.

Example 18 illustrates a limit to the number of atoms forming the R" bridge. Apparently, the steric effect of inserting two carbon atoms and two alkyl silicon groups was too great and caused the catalyst to shift in such a way as to block the production of propylene.

It is known that the mole fraction of inversions in the isotactic polymer chain does correlate with the melting points. When the mole fractions are plotted against the log $T_m$, the points fit a straight line through the regions tested in the Examples. The equation for the line is mole fraction of inversions=$-0.5 \log T_m$(°C)+1.094. As the number of inversions increase, the melting point of the polymer decreases. The number of inversions also vary as the R" bridge is changed.

Having described a few embodiments of the present invention, it will be understood by those skilled in the art that modifications and adoptions may be made without departing from the scope of the present invention.

I claim:

1. A catalyst system for polymerization of propylene having increased molecular weight and melting point comprising
   (a) a chiral, stereorigid metallocene catalyst described by the formula:

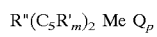

wherein ($C_5R'_m$) is a cyclopentadienyl or substituted cyclopentadienyl; R' is hydrogen or hydrocarbyl radical having from 1–20 carbon atoms, each R' may be the same or different; R" is a silicon hydrocarbyl radical and acts as an interannular bridge between the two ($C_5R'_m$) rings; Q is a hydrocarbon radical chosen from the group consisting of an aryl, alkyl, alkenyl, alkylaryl and arylalkyl radical having 1–20 carbon atoms or is a halogen; Me is a group 4b, 5b, or 6b metal as designated in the Periodic Table of Elements; $0 \leq m \leq 4$; and $0 \leq p < 3$; and
   (b) an organoaluminum compound.

2. A catalyst system as in claim 1 wherein the organoaluminum compound is alumoxane represented by the formula:

or

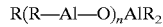

wherein R is an alkyl group with 1–5 carbons and n is an integer from 1 to 20.

3. A catalyst system as in claim 1 wherein Me is titanium, zirconium or hafnium.

4. A catalyst system as in claim 3 wherein Me is zirconium.

5. A catalyst system as in claim 1 wherein R" is an alkyl silyl or cycloalkyl silyl radical.

6. A catalyst system as in claim 5 wherein R" is dimethyl silicon.

7. A catalyst system as in claim 5 wherein R" is cyclopropyl silicon.

8. A catalyst system as in claim 1 wherein $C_pR'_m$ is indenyl.

9. A catalyst system as in claim 1 wherein Q is a halogen and $p$ is 2.

10. A catalyst system as in claim 1 wherein the metallocene catalyst is dimethylsilylbis-(indenyl)zirconium dichloride.

11. A catalyst system as in claim 1 wherein the metallocene catalyst is cyclopropylsilylbis-(indenyl)zirconium dichloride.

12. A catalyst system as in claim 9 wherein Q is chlorine.

* * * * *